United States Patent [19]

Böshagen et al.

[11] Patent Number: 5,051,407
[45] Date of Patent: Sep. 24, 1991

[54] METHODS FOR TREATING VIRUSES IN PATIENTS BY ADMINISTERING 2-HYDROXYMETHYLENE-3,4,5-TRIHYDROXYPIPERIDINES

[75] Inventors: Horst Böshagen, Haan; Bodo Junge, Wuppertal; Günther Kinast, Wuppertal; Matthias Schüller, Wuppertal; Jürgen Stoltefuss; Arnold Paessens, both of Haan, all of Fed. Rep. of Germany

[73] Assignee: Bayer Aktiengesellschaft, Leverkusen, Fed. Rep. of Germany

[21] Appl. No.: 259,932

[22] Filed: Oct. 19, 1988

[30] Foreign Application Priority Data

Nov. 5, 1987 [DE] Fed. Rep. of Germany ....... 3737523

[51] Int. Cl.$^5$ ........................................... A61K 31/445
[52] U.S. Cl. ...................................... 514/24; 514/315; 514/316; 514/319; 514/325; 514/326; 514/328
[58] Field of Search .................. 514/24, 315, 316, 319, 514/325, 326, 328

[56] References Cited

U.S. PATENT DOCUMENTS

| 4,260,622 | 4/1981 | Junge et al. | 514/315 |
|---|---|---|---|
| 4,293,551 | 10/1981 | Kinast et al. | 514/318 |
| 4,328,233 | 5/1982 | Böshagen et al. | 514/319 |
| 4,407,809 | 10/1983 | Junge et al. | 514/319 |
| 4,894,366 | 1/1990 | Okuhara et al. | 514/63 |

FOREIGN PATENT DOCUMENTS 3024901 1/1982 Fed. Rep. of Germany .

OTHER PUBLICATIONS

Nature, vol. 322, Jul. 1986, "Pathogenesis of Lentivirus Infections", pp. 130–136.
Antimicrobial Agents & Chemotherapy, Sep. 1987, pp. 1369–1374, vol. 31, No. 9, "Visna Virus as an In Vitro . . . 2′,3′-Dideoxynucleosides".
Journal of Virology, May 1987, pp. 1325–1331, vol. 61, No. 5, "Visna Virus Exhibits . . . Syndrome Retrovirus".
Proc. Natl. Acad. Sci. USA, vol. 86, pp. 414–418, Jan. 1989, Biochemistry, "Characterization of a cDNA . . . Protein".
"A Comparative Analysis of the . . . Syndrome Lentiviruses", 1986, pp. 339–343.
Science, vol. 229, "Cis- and Trans-Acting Transcriptional Regulation of the Visna Virus", pp. 482–485.
Cell, vol. 42, pp. 369–382, Aug. 1985, "Nucleotide Squences of the Visna Lentivirus: Relationship to the AIDS Virus".
Science, vol. 227, Jan. 1985, pp. 173–177, "Sequence Homology . . . a Pathogenic Lentivirus".
Proc. Natl. Acad. Sci., vol. 82, pp. 7096–7100, Oct. 1985; Medical Sciences; 3′-Azido-3′-deoxythymidine (BW A509U); An Antiviral Agent that Inhibits the Infectivity and Cytopathic Effect of Human T-Lymphotropic Virus Type III/Lymphadenopathy-Associated Virus in Vitro; Hiroaki Mitsuya et al.
Macmillan Journals Ltd., 1987, vol. 325, No. 6107, pp. 773–778; Strategies for Antiviral Therapy in AIDS; Hiroaki Mitsuya et al.
Drugs Reviews; vol. 6, Dec. 1987, Clinical Pharmacy, pp. 927–939; Development of Antiviral Agents for the Treatment of Human Immunodeficiency Virus Infection; Teresa A. Tartaglione and Ann C. Collier.
The Lancet, May 27, 1989; p. 1206; Anti-HIV Activity of Castanospermine Analogues.
Fifteenth Edition, The Merck Manual of Diagnosis and Therapy, Berkow et al., Published by Merck Sharp & Dohme Research Laboratories, Rahway, N.J., 1987, pp. 158–168.

Primary Examiner—Ronald W. Griffin
Attorney, Agent, or Firm—Sprung Horn Kramer & Woods

[57] ABSTRACT

A method for treating a viral infection in a human or animal patient comprising administering to such patient an antivirally effective amount of a substituted hydroxypiperidine, namely a 2-hydroxymethylene-3,4,5-trihydroxypiperidine.

11 Claims, No Drawings

METHODS FOR TREATING VIRUSES IN PATIENTS BY ADMINISTERING 2-HYDROXYMETHYLENE-3,4,5-TRIHYDROXYPIPERIDINES

BACKGROUND OF THE INVENTION

1. Field of the Invention

The invention relates to methods for treating human and animal patients suffering from viruses by administering to such patients a 2-Hydroxymethylene, 3,4,5-trihydroxypiperidine.

2. Background Information

It has been disclosed that desoxynojirimycin derivatives are glucosidase inhibitors (EP 947; EP 8,058; EP 34,784; DE 2,848,117). Moreover, it is known that some desoxynojirimycin derivatives have herbicidal actions (DE 3,024,901).

SUMMARY OF THE INVENTION

It has now been found that 2-Hydroxymethylene-branched 3,4,5-trihydorxypiperidines of the general formula (I)

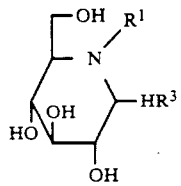

(I)

in which
$R^1$ stands for hydrogen and
$R^3$ stands for an optionally substituted straight-chain, branched or cyclic, saturated or unsaturated hydrocarbon radical which is optionally interrupted by heteroatoms such as O or S, an optionally substituted aromatic radical or an optionally substituted heterocyclic radical, have good antiviral action.

DETAILED DESCRIPTION OF THE INVENTION

Preferably, $R^3$ denotes $C_1$-$C_{30}$-alkyl, $C_2$-$C_{18}$-alkenyl, $C_2$-$C_{18}$-alkinyl, $C_3$-$C_{12}$-cycloalkyl, $C_3$-$C_{12}$-cycloalkenyl, $C_3$-$C_{12}$-cycloalkadienyl, $C_3$-$C_{12}$-bicycloalkyl, $C_3$-$C_{12}$-bicycloalkenyl, $C_3$-$C_{12}$-bicycloalkadienyl, $C_3$-$C_{12}$-tricycloalkyl, $C_3$-$C_{12}$-tricycloalkenyl or $C_3$-$C_{12}$-tricycloalkadienyl, phenyl, naphthyl, $C_3$-$C_7$-heterocyclyl having 1 to 4 carbon atoms from the series comprising N, O or S, onto which can be condensed a benzene radical, where the radicals mentioned can carry 1 to 5 substituents.

Suitable substituents for phenyl, naphthyl and heterocyclyl are halogen, in particular chlorine, bromine and fluorine, $C_1$-$C_4$-alkyl, halogeno-$C_1$-$C_4$-alkyl, $C_1$-$C_4$-alkoxy, $C_1$-$C_4$-alkylmercapto, $C_1$-$C_4$-alkylsulphonyl, nitro, cyano, di-$C_1$-$C_{12}$-alkylamino, di-$C_1$-$C_{12}$-alkylaminosulphonyl, di-$C_1$-$C_{12}$-dialkylaminocarbonyl, pyrrolidino, pyrrolidinosulphonyl, pyrrolidinocarbonyl, piperidino, piperidinosulphonyl, piperidinocarbonyl, morpholino, morpholinosulphonyl, morpholinocarbonyl, N'-$C_1$-$C_4$-alkylpiperazino, N'-$C_1$-$C_4$-alkylpiperazinosulphonyl, N'-$C_1$-$C_4$-alkylpiperazinocarbonyl, pyridyl, thienyl, imidazolyl, isoxazolyl, thiazolyl, glucopyranosyl and ribofuranosyl.

Substituents of the remaining definitions of $R^3$ which may be mentioned are, for example, $C_1$-$C_4$-alkyl, $C_1$-$C_4$-alkoxy, $C_1$-$C_4$-alkylmercapto, halogen, in particular fluorine, chlorine and bromine, di-$C_1$-$C_{12}$-alkylamino, pyrrolidino, piperidino, morpholino, N'-$C_1$-$C_4$-alkylpiperazino, and phenyl or naphthyl, each of which are optionally substituted by halogen, in particular fluorine, chlorine and bromine, $C_1$-$C_4$-alkyl, $C_1$-$C_4$-alkoxy, $C_1$-$C_4$-alkylmercapto, $C_1$-$C_4$-alkylsulphonyl, nitro, $C_1$-$C_4$-alkoxycarbonyl, di-$C_1$-$C_{12}$-alkylaminocarbonyl, di-$C_1$-$C_{12}$-alkylaminosulphonyl, pyridyl, thienyl, imidazolyl, isoxazolyl, thiazolyl, glucopyranosyl and ribofuranosyl.

The alkyl radicals $R^3$ can moreover carry $C_3$-$C_{12}$-cycloalkyl, $C_3$-$C_{12}$-cycloalkenyl, $C_3$-$C_{12}$-cycloalkadienyl, $C_3$-$C_{12}$-bicycloalkyl, $C_3$-$C_{12}$-bicycloalkenyl, $C_3$-$C_{12}$-bicycloalkadienyl, $C_3$-$C_{12}$-tricycloalkyl, $C_3$-$C_{12}$-tricycloalkenyl or $C_3$-$C_{12}$-tricycloalkadienyl as substituents.

In preferred compounds of the formula (I), $R^1$ denotes $C_1$-$C_{18}$-alkyl, optionally substituted by 1 to 5 halogen atoms, $C_3$-$C_{10}$-alkenyl, $C_3$-$C_{10}$-alkinyl, $C_3$-$C_7$-cycloalkyl or phenyl which is optionally substituted by halogen, $C_1$-$C_4$-alkyl, $C_1$-$C_4$-alkoxy or nitro.

These compounds are known from DE 2,848,117.

Compounds of the general formula (I) in which
$R^1$ stands for hydrogen or for an optionally substituted, straight-chain, branched or cyclic, saturated or unsaturated hydrocarbon radical, or for an optionally substituted aromatic or heterocyclic radical and
$R^3$ stands for —H, OH, —OR$^5$, —SH, SR$^5$, —NH$_2$, —NHR$^5$,

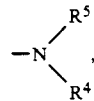

NH$_2$CH$_2$—, NHR$^5$—CH$_2$—, NR$^5$R$^4$—CH$_2$—, —COOH, —COOR$^5$, HO—CH$_2$—, R$^5$CO—NHCH$_2$—, R$^5$CO—NR$^4$CH$_2$—, R$^5$SO$_2$NHCH$_2$—, R$^5$SO$_2$—NR$^4$CH$_2$—,

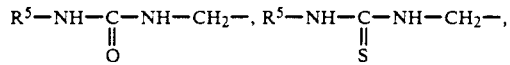

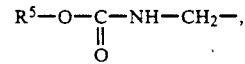

—SO$_3$H, —CN, —CONH$_2$, CONHR$^5$ or CONR$^5$R$^4$
where
$R^5$ and $R^4$ can assume the meanings previously mentioned for $R^1$,
and where for the case in which $R^3$=H or OH, $R^1$ stands for an optionally substituted, straight-chain, branched or cyclic, saturated or unsaturated hydrocarbon radical or for an optionally substituted aromatic or heterocyclic radical (i.e., $R^1$ is not H) likewise have a good antiviral action.

Preferably, $R^1$, $R^5$ and $R^4$ denote an alkyl radical having 1 to 30, in particular 1 to 18 C atoms; an alkenyl radical or alkinyl radical having 2 to 18, in particular 3 to 10 C atoms; a mono-, bi- or tricyclic radical having 3 to 10 C atoms, which can be saturated or mono-unsaturated or diunsaturated, an aryl radical having 6 to 10 C atoms, a heterocyclic radical having 3 to 8, in particular 3 to 6 ring members, which can contain 1, 2, 3 or 4 heteroatoms, in particular N, O or S and onto which can be condensed a benzene ring or an additional heterocycle of the type mentioned, where the radicals mentioned can carry 1 to 5, in particular 1, 2 or 3 substituents.

Substituents for alkyl which may be mentioned are, for example: hydroxyl or alkoxy preferably having 1 to 4 carbon atoms, in particular methoxy and ethoxy; acyloxy, where the acyl radical is derived from aliphatic carboxylic acids having 1 to 7 C atoms, aromatic carboxylic acids, in particular phenylcarboxylic acids, which can be substituted in the phenyl radical by —OH, -halogen, in particular F, Cl, Br, $C_1$–$C_4$-alkyl, $C_1$–$C_4$-alkoxy, nitro and/or amino, heterocyclic carboxylic acids which are derived from 5- or 6-membered heterocycles which contain 1 to 3 heteroatoms (N, O, S) and can be substituted in the heterocyclic ring by $C_1$–$C_4$-alkyl, chlorine, bromine or amino; amino, monoalkylamino and dialkylamino preferably having 1 to 4 carbon atoms per alkyl radical, in particular monomethylamino, monoethylamino, dimethylamino and diethylamino, monoacylamino, where the acyl radical is derived from aliphatic carboxylic acids having 1 to 7 C atoms, aromatic carboxylic acids, in particular phenylcarboxylic acids which can be substituted in the phenyl radical by —OH, -halogen, in particular F, Cl, Br, $C_1$–$C_4$-alkyl, $C_1$–$C_4$-alkoxy, nitro and/or amino, heterocyclic carboxylic acids which are derived from 5- or 6-membered heterocycles containing 1 to 3 heteroatoms (N, O, S) and which can be substituted in the heterocyclic ring by $C_1$–$C_4$-alkyl, chlorine, bromine or amino;

Mercapto, alkylthio preferably having 1 to 4 carbon atoms, in particular methylthio and ethylthio; halogen, preferably fluorine, chlorine and bromine; alkylcarbonyl preferably having 1 to 4 carbon atoms in the alkyl radical; carboxyl, nitro, cyano, the aldehyde function, the sulphonic acid group; and also heterocyclic radicals of the abovementioned type, in particular heterocyclic radicals also derived from sugars, very particularly hexoses or pentoses, which can be directly connected with the alkyl radical via a ring atom or via an —O—, —S— or —NH bridge.

Examples of heterocyclic substituents of the alkyl radicals are: phthalimido, pyridyl, thienyl, furyl, isoxazolyl, thiazolyl, glucopyranosyl, ribofuranosyl, oxiranyl and the like.

Additionally suitable as substituents of the alkyl radicals are aromatic radicals such as naphthyl and in particular phenyl, which can carry one or more, preferably 1 to 3 identical or different substituents from the series comprising —OH, —$NH_2$, $C_1$–$C_4$-alkyl-NH-, $C_1$–$C_4$-dialkyl-N-, $C_1$–$C_4$-alkoxy, $NO_2$—, —CN, —COOH, —COO-alkyl ($C_1$–$C_4$), $C_1$–$C_6$-alkyl, halogen, in particular fluorine, chlorine or bromine, $C_1$–$C_4$-alkylthio, —SH, $C_1$–$C_4$-alkylsulphonyl, —$SO_3H$, —$SO_2$—$NH_2$, —$SO_2$—NH-alkyl ($C_1$–$C_4$).

The alkyl radical can also carry a mono-, bi- or tricyclic substituent preferably having 3 to 10 carbon atoms, which in turn can be substituted by hydroxyl, amino, halogen, in particular fluorine, chlorine, bromine, or —COOH.

The alkyl radical preferably carries substituents such as hydroxyl or alkoxy having 1 to 4 carbon atoms; mercapto or alkylthio having 1 to 4 carbon atoms, halogen, nitro, amino, monoalkylamino having 1 to 4 C atoms and acylamino, where the acyl radical is derived from aliphatic carboxylic acids having 1 to 6 C atoms.

For the cyclic mono-, bi- or tricyclic radicals $R^1$, $R^5$ and $R^4$, possible substituents are those mentioned for the alkyl radicals.

The aryl radicals can carry one or more, preferably 1 to 3 identical or different substituents. Substituents which may be mentioned are, for example: alkyl having 1 to 10 C atoms, which in turn can be further substituted, for example, by chlorine, nitro or cyano; optionally substituted alkenyl radicals having 1 to 10 carbon atoms; hydroxyl, alkoxy preferably having 1 to 4 carbon atoms; amino, monoalkylamino and dialkylamino preferably having 1 to 4 carbon atoms per alkyl radical; mercapto, alkylthio preferably having 1 to 4 carbon atoms, carboxyl, carbalkoxy preferably having 1 to 4 carbon atoms; the sulphonic acid group, alkylsulphonyl preferably having 1 to 4 carbon atoms, arylsulphonyl, preferably phenylsulphonyl; aminosulphonyl, alkylaminosulphonyl and dialkylaminosulphonyl having 1 to 4 carbon atoms per alkyl group, preferably methylsulphonyl and dimethylaminosulphonyl; nitro, cyano or the aldehyde group, alkylcarbonylamino preferably having 1 to 4 carbon atoms; alkylcarbonyl having 1 to 4 carbon atoms; benzoyl, benzylcarbonyl and phenethylcarbonyl, where the lastmentioned alkyl, phenyl, benzyl and phenethyl radicals can in turn again be substituted, for example, by chlorine, nitro or hydroxyl.

The heterocyclic radicals $R^1$ are preferably derived from heteroparaffinic, heteroaromatic or heteroolefinic 5- or 6-membered rings preferably having 1 to 3 identical or different heteroatoms. Heteroatoms are oxygen, sulphur or nitrogen. These ring systems can carry additional substituents such as, for example, hydroxyl-, amino- or $C_1$–$C_4$-alkyl groups or benzene nuclei or additional, preferably 6-membered, heterocyclic rings of the type mentioned can be fused onto them.

Particularly preferred heterocyclic radicals are derived, for example, from furan, pyran, pyrrolidine, piperidine, pyrazole, imidazole, pyrimidine, pyridazine, triazine, pyrrole, pyridine, benzimidazole, quinoline, isoquinoline or purine.

In the compounds of the formula I, $R^3$ preferably stands for —H, —OH, —$SO_3H$, —CN, —$CH_2NH_2$, —$CH_2$NH-($C_1$–$C_{14}$-Alkyl),

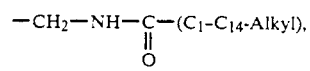

—$CH_2$—NH—$SO_2$-($C_1$ to $C_{14}$)-Alkyl, —$CH_2$—NH—$SO_2$-Phenyl, $R^5$—NH—C—NH—$CH_2$—,

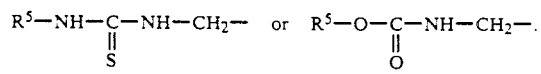

Very particularly preferably, $R^3$ stands for —H, —$SO_3H$, —CN or

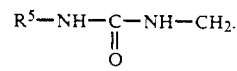

These compounds are known from EP 947.

Furthermore to be mentioned are compounds of the general formula (I) in which $R^1$ stands for

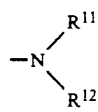

wherein
R¹¹ denotes hydrogen, -formyl, —R¹⁴, —COR¹⁴, CO₂R¹⁴, CONH₂, CONHR¹⁴, CONR¹⁴R¹⁵, CSR¹⁴, CSNH₂, CSNHR¹⁴, CSNR¹⁴R¹⁵, SO₃H or SO₂R¹⁴,
R¹² denotes hydrogen or R¹⁴ or
R¹¹ and R¹² together denote the grouping

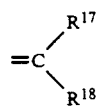

R³ denotes hydrogen, hydroxyl, OR¹⁴, mercapto, SR¹⁴, amino, NHR¹⁴, NR¹⁴R¹⁵, cyano, carboxyl, CO₂R¹⁴, carboamido, CONHR¹⁴, CONR¹⁴R¹⁵, aminomethyl, CH₂NHR¹⁴, CH₂NR¹⁴R¹⁵, CH₂-NR¹⁴COR¹⁵, CH₂NR¹⁴SO₂R¹⁵, sulpho, hydroxymethyl, CH₂OR¹⁴ or CH₂OCOR¹⁴, and
R¹⁴ and R¹⁵ independently of one another denote an optionally substituted, straight-chain, branched or cyclic, saturated or unsaturated aliphatic hydrocarbon radical or an optionally substituted aromatic or heterocyclic radical, where two radicals R¹⁵, R¹⁷ and R¹⁸ can also be bonded with one another, and
R¹⁷ and R¹⁸ independently of one another denote hydrogen or R¹⁵.

Preferably, R¹⁴ and R¹⁵ denote alkyl having 1 to 30, in particular 1 to 18 C atoms, alkenyl or alkinyl having 2 to 18, in particular 3 to 10, C atoms, mono-, bi- or tricycloalkyl, -alkenyl or -alkadienyl having 3 to 10 C atoms, aryl having 6 to 10 C atoms, a heterocyclic radical having 3 to 8, in particular 3 to 6, ring members, which can contain 1, 2, 3 or 4 heteroatoms, in particular N, O or S and onto which can be condensed a benzene ring or an additional heterocycle of the type mentioned, where the radicals mentioned can carry 1 to 5, in particular 1, 2 or 3 substituents.

Substituents for alkyl which may be mentioned are, for example, hydroxyl, alkoxy preferably having 1 to 4 carbon atoms, in particular methoxy and ethoxy; alkylcarbonyloxy having 1 to 7 C atoms; benzoyloxy, heterocyclyl and carbonyloxy which are optionally substituted by —OH, -halogen, in particular F, Cl, Br, C₁-C₄-alkyl, C₁-C₄-alkoxy, nitro and/or amino and which are derived from 5- or 6-membered heterocycles, which contain 1 to 3 hetero atoms (N, O, S) and can be substituted in the heterocyclic ring by C₁-C₄-alkyl, chlorine, bromine or amino; amino, monoalkylamino and dialkylamino preferably having 1 to 4 carbon atoms per alkyl radical, in particular monomethylamino, monoethylamino, dimethylamino and diethylamino; monoacylamino, where the acyl radical is derived from aliphatic carboxylic acids having 1 to 7 C atoms, aromatic carboxylic acids, in particular phenylcarboxylic acids, which can be substituted in the phenyl radical by —OH, -halogen, in particular F, Cl, Br, C₁-C₄-alkyl, C₁-C₄-alkoxy, nitro and/or amino; heterocyclic carboxylic acids which are derived from 5- or 6-membered heterocycles which contain 1 to 3 heteroatoms (N, O, S) and can be substituted in the heterocyclic ring by C₁-C₄-alkyl, chlorine, bromine or amino; mercapto, alkylthio preferably having 1 to 4 carbon atoms, in particular methylthio and ethylthio; halogen, preferably fluorine, chlorine and bromine; alkylcarbonyl preferably having 1 to 4 carbon atoms in the alkyl radical; carboxyl, nitro, cyano, formyl, sulpho; heterocyclic radicals of the above-mentioned type and radicals of sugars, in particular heterocyclic radicals derived from hexoses or pentoses, which can be connected directly via a ring atom or via an —O—, —S— or —NH— bridge with the alkyl radical.

Examples of the previously mentioned heterocycles are phthalimido, pyridyl, thienyl, furyl, isoxazolyl, thiazolyl, glucopyranosyl, ribofuranosyl and oxiranyl.

The alkyl radical can also carry a mono-, bi- or tricyclic substituent preferably having 3 to 10 carbon atoms, which in turn can be substituted by hydroxyl, amino, halogen, in particular fluorine, chlorine, bromine or —COOH.

The alkyl radical preferably carries substituents such as hydroxyl, alkoxy having 1 to 4 carbon atoms, mercapto, alkylthio having 1 to 4 carbon atoms, halogen, nitro, amino, monoalkylamino having 1 to 4 C atoms and acylamino, where the acyl radical is derived from aliphatic carboxylic acids having 1 to 6 C atoms.

For the cyclic mono-, bi- or tricyclic radicals R¹, possible substituents are those mentioned for the alkyl radicals.

The aryl radicals R¹⁴ and R¹⁵ can carry one or more, preferably 1 to 3, identical or different substituents.

Substituents which may be mentioned are, for example:

alkyl having 1 to 10 C atoms, which in turn can again be substituted, for example, by chlorine, nitro or cyano; optionally substituted alkenyl radicals having 2 to 10 carbon atoms; hydroxyl, alkoxy preferably having 1 to 4 carbon atoms; amino, monoalkylamino and dialkylamino preferably having 1 to 4 carbon atoms per alkyl radical; mercapto, alkylthio preferably having 1 to 4 carbon atoms, carboxyl, carbalkoxy preferably having 1 to 4 carbon atoms, the sulphonic acid group, alkylsulphonyl preferably having 1 to 4 carbon atoms, arylsulphonyl, preferably phenylsulphonyl, aminosulphonyl, alkylaminosulphonyl and dialkylaminosulphonyl having 1 to 4 carbon atoms per alkyl group, preferably methylaminosulphonyl and dimethylaminosulphonyl; nitro, cyano, formyl, alkylcarbonylamino preferably having 1 to 4 carbon atoms; alkylcarbonyl having 1 to 4 carbon atoms, benzoyl, benzylcarbonyl and phenethylcarbonyl, where the lastmentioned alkyl, phenyl, benzyl and phenethyl radicals can in turn again be substituted, for example, by chlorine, nitro or hydroxyl. Aryl is preferably phenyl and naphthyl here.

The heterocyclic radicals R¹⁴ and R¹⁵ are preferably derived from heteroparaffinic, heteroaromatic or heteroolefinic 5- or 6-membered rings preferably having 1 to 3 identical or different heteroatoms from the series comprising oxygen, sulphur or nitrogen. These ring systems can carry additional substituents such as hydroxyl-, amino- or C₁-C₄-alkyl groups or benzene nuclei or additional, preferably 6-membered, heterocyclic rings of the type mentioned can be fused onto them.

Particularly preferred heterocyclic radicals are derived from furan, pyran, pyrrolidine, piperidine, pyrazole, imidazole, pyrimidine, pyridazine, pyrazine, triazine, pyrrole, pyridine, benzimidazole, quinoline, isoquinoline and purine.

For preferred compounds within the formula (I), $R^3$ stands for hydrogen, hydroxyl, sulpho, cyano, aminomethyl, $C_1-C_6$-alkylaminomethyl and $C_1-C_6$-alkylcarbonylaminomethyl. $R^4$ preferably denotes hydroxymethyl, hydroxy($C_1-C_6$-alkyl)-methyl, $C_1-C_7$-alkyl and $C_1-C_5$-alkoxymethyl.

Very particularly preferred compounds of the formula (I) are those in which
$R^1$ stands for

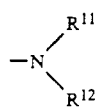

wherein
$R^{11}$ denotes hydrogen, $C_1-C_4$-alkyl, $C_1-C_4$-alkoxy, $C_1-C_4$-alkylsulphonyl, $C_1-C_4$-alkylcarbonyl or -phenyl, in particular hydrogen, methyl, ethyl, acetyl, methylsulphonyl, propionyl or phenyl, $R^{12}$ denotes hydrogen, $C_1-C_{12}$-alkyl or $C_2-C_4$ alkenyl which is optionally substituted by hydroxyl, $C_1-C_4$-alkoxy, carboxyl, $C_5-C_7$-cycloalkyl or phenylsulphonylamino, phenyl which is optionally substituted in the phenyl ring by halogen, in particular fluorine or chlorine, $C_1-C_4$-alkyl, hydroxyl, di-$C_1-C_4$-alkylamino or $C_1-C_4$-alkoxy, phenyl-$C_1-C_4$-alkyl or benzoylmethyl, $C_5-C_7$-cycloalkyl, furylmethyl, pyridylmethyl or diphenylmethyl or $R^1$ and $R^2$ together denote a grouping

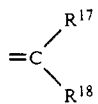

wherein
$R^{18}$ denotes hydrogen, $C_1-C_{12}$-alkyl which is optionally substituted by hydroxyl, $C_1-C_4$-alkoxy or phenylsulphonylamino, $C_5-C_7$-cycloalkyl, $C_2-C_{12}$-alkenyl, carboxyl, phenyl which is optionally substituted by halogen, in particular fluorine and chlorine, $C_1-C_4$-alkyl, hydroxyl, nitro, di-$C_1-C_4$-alkylamino, $C_1-C_4$-alkoxy or $C_1-C_4$-carboxyl, phenyl-$C_1-C_4$-alkyl or phenyl-$C_1-C_4$-benzoyl, furyl, pyridyl or together with $R_7$ and the double bonded C atom denote a cyclopentane or cyclohexane ring and
$R^{17}$ has the meaning of $R^{11}$, and
$R^3$ denotes hydrogen, $C_1-C_6$-alkylcarbonylaminomethyl, phenylcarbonylaminomethyl, phenylsulphonylaminomethyl, $C_1-C_4$-alkoxycarbonyl and $C_1-C_6$-alkylaminocarbonyl.

The following active compounds may be mentioned as very particularly preferred:
These compounds are, for example, known from European Patent Application 8,058.

Antiviral action is likewise shown by compounds of the general formula (I), in which $R^1$ stands for

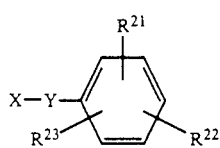

wherein
X stands for a straight-chain or branched saturated or unsaturated hydrocarbon radical,
Y stands for oxygen or sulphur and
$R^{21}$, $R^{22}$ and $R^{23}$ are identical or different and independently of one another stand for hydrogen, halogen, alkyl, aryl, alkoxy, aroxy, alkylthio, nitro, amino, hydroxyl, cyano, alkylamino and dialkylamino, acylamino, acyloxy, carboxyl, carbalkoxy, alkylcarbonyl, formyl or an optionally substituted sulphonamide radical.

The invention preferably relates to those compounds of the formula (I) in which X in $R^1$ denotes a saturated or monounsaturated or polyunsaturated alkyl radical having 2 to 10, preferably 2 to 5 C atoms and Y, $R^{21}$, $R^{22}$ and $R^{23}$ have the abovementioned meaning. $R^{21}$, $R^{22}$ and $R^{23}$ preferably denote hydrogen, alkyl, alkoxy or halogen.

These compounds are known from DE 3,007,078.

The following active compounds may be mentioned as very particularly preferred:
N-β-Phenoxyethyl-1-desoxynojirimycin
N-(5-Phenoxypentyl)-1-desoxynojirimycin
N-(4-Phenoxybutyl)-1-desoxynojirimycin
N-[β-(2,6-Dimethylphenoxy)ethyl]-1-desoxynojirimycin
N-[γ-(2,6-Dimethoxyphenoxy)propyl]-1-desoxynojirimycin
N-[β-(2,4-Dichlorophenoxy)ethyl]-1-desoxynojirimycin
N-(γ-Phenoxypropyl)-1-desoxynojirimycin
N-(4-Phenoxy-trans-buten-2-yl)-1-desoxynojirimycin hydrate
N-(p-Methoxyphenyloxy-trans-buten-2-yl)-1-desoxynojirimycin
N-[(4-Carbethoxyphenyloxy)buten-2-yl]-1-desoxynojirimycin
N-[β-(4-Methoxyphenoxy)ethyl]-1-desoxynojirimycin
N-[β-(4-Chlorophenoxy)ethyl]-1-desoxynojirimycin
N-[β-(4-Cyanophenoxy)ethyl]-1-desoxynojirimycin
N-[β-(3-Methylphenoxy)ethyl]-1-desoxynojirimycin
N-(β-Phenylthioethyl)-1-desoxynojirimycin
N-[β-(4-Methylphenylthio)ethyl]-1-desoxynojirimycin
N-[4-(4-Methylphenylthio)buten-2-yl]-1-desoxynojirimycin
N-[4-(4-Chlorophenylthio)buten-2-yl]-1-desoxynojirimycin
N-[4-(4-tert.-Butylphenylthio)buten-2-yl]-1-desoxynojirimycin
N-[4-(4-Methylphenylthio)buten-2-yl]-1-desoxynojirimycin
N-[4-(4-Phenylphenoxy)buten-2-yl]-1-desoxynojirimycin
N-[β-(4-Acetamidophenoxy)ethyl]-1-desoxynojirimycin
N-[β-(4-Ethoxycarbonylphenoxy)ethyl]-1-desoxynojirimycin
N-[β-(4-Formylphenoxy)ethyl]-1-desoxynojirimycin
N-[β-(4-Hydroxyphenoxy)ethyl]-1-desoxynojirimycin
N-[β-(3-Ethoxycarbonylphenoxy)ethyl]-1-desoxynojirimycin
N-[4-(4-Acetamidophenoxy)buten-2-yl]-1-desoxynojirimycin hydrate
N-[β-(4-Aminomethylphenoxy)ethyl]-1-desoxynojirimycin
N-[β-(4-Hydroxymethylphenoxy)ethyl]-1-desoxynojirimycin N-[4-(4-Aminophenoxy)but-2-en-yl]-1-desoxynojirimycin
N-[β-(4-Aminophenoxy)ethyl]-1-desoxynojirimycin
N-[β-(4-Hydroxycarbonylphenoxy)ethyl]-1-desoxynojirimycin
N-[β-(3-Hydroxycarbonylphenoxy)ethyl]-1-desoxynojirimycin
N-[β-(4-tert.-Butylphenylthio)ethyl]-1-desoxynojirimycin
N-(4-Phenylthiobuten-2-yl)-1-desoxynojirimycin
N-[β-(4-Cyanomethylphenoxy)ethyl]-1-desoxynojirimycin
N-[β-(4-Aminoethylphenoxy)ethyl]-1-desoxynojirimycin
N-[β-(4-Succinimidyloxycarbonyl)ethyl]-1-desoxynojirimycin
N-[β-(4-Carbamoylphenoxy)ethyl]-1-desoxynojirimycin
N-[β-(4-Morpholinocarbonylphenoxy)ethyl]-1-desoxynojirimycin
N-[2-(4-Phenylcarbamoylphenoxy)ethyl]-1-desoxynojirimycin
N-[2-(4-Phenylphenoxy)ethyl]-1-desoxynojirimycin
2-Hydroxymethyl-3,4,5-trihydroxy-6-methylpiperidine
2-Hydroxymethyl-3,4,5-trihydroxy-6-ethylpiperidine
2-Hydroxymethyl-3,4,5-trihydroxy-6-propylpiperidine
2-Hydroxymethyl-3,4,5-trihydroxy-6-n-butylpiperidine
2-Hydroxymethyl-3,4,5-trihydroxy-6-n-pentylpiperidine
2-Hydroxymethyl-3,4,5-trihydroxy-6-n-octylpiperidine
2-Hydroxymethyl-3,4,5-trihydroxy-6-phenylpiperidine
2-Hydroxymethyl-3,4,5-trihydroxy-6-n-heptylpiperidine of the D-gluco configuration and N-Amino-1-desoxynojirimycin
N-(Benzylideneamino)-1-desoxynojirimycin
N-(2-Hydroxy-3-methoxybenzylideneamino)-1-desoxynojirimycin
N-(3-Nitrobenzylidene)amino-1-desoxynojirimycin
N-(3-Phenylpropylidene)amino-1-desoxynojirimycin
N-(4-Methylbenzylidene)amino-1-desoxynojirimycin
N-(4-Methoxybenzylidene)amino-1-desoxynojirimycin
N-(3-Cyclohexenyl)methyleneamino-1-desoxynojirimycin
N-Undecylideneamino-1-desoxynojirimycin
N-Heptylideneamino-1-desoxynojirimycin
N-(Furfurylideneamino)-1-desoxynojirimycin
N-(Thenylideneamino)-1-desoxynojirimycin
N-(3-Pyridylmethyleneamino)-1-desoxynojirimycin
N-(4-Chlorobenzylideneamino)-1-desoxynojirimycin
N-(2-Methylthiobenzylideneamino)-1-desoxynojirimycin
N-(Benzylamino)-1-desoxynojirimycin
N-(Acetamido)-1-desoxynojirimycin
N-(Heptylamino)-1-desoxynojirimycin
N-(Dimethylamino)-1-desoxynojirimycin
N-(Dioctylamino)-1-desoxynojirimycin
N-(2-Vinylsulphonylethyl)-1-desoxynojirimycin
N-Undecen-10-yl-1-desoxynojirimycin
1-(N'-5-Cyanopentylureidomethyl)-1-desoxynojirimycin
N-(Hexa-2,4-dienyl)-1-desoxynojirimycin
N-Methyl-1-desoxynojirimycin
N-Butyl-1-desoxynojirimycin
N-Ethyl-1-desoxynojirimycin
N-Propyl-1-desoxynojirimycin
N-Isobutyl-1-desoxynojirimycin
N-Heptyl-1-desoxynojirimycin
N-Benzyl-1-desoxynojirimycin
N-(2-Pyridylmethyl)-1-desoxynojirimycin
N-(2-Hydroxyethyl)-1-desoxynojirimycin
N-(2,3-Dihydroxypropyl)-1-desoxynojirimycin
N-[2-(s-β-D-Glucopyranosylthio)ethyl]-1-desoxynojirimycin
N-(2,3-Epoxypropyl)-1-desoxynojirimycin
N-[3-Phthalimidopropyl]-1-desoxynojirimycin
N-(3-Aminopropyl)-1-desoxynojirimycin
N-(1-Desoxynojirimycin-yl)acetic acid
N-o-Nitrobenzyl-1-desoxynojirimycin
N-o-Carboxybenzyl-1-desoxynojirimycin
N-p-Sulphobenzyl-1-desoxynojirimycin
N-Phenethyl-1-desoxynojirimycin
N-Pentyl-1-desoxynojirimycin
N-Hexyl-1-desoxynojirimycin
N-Octyl-1-desoxynojirimycin
N-Nonyl-1-desoxynojirimycin
N-Decyl-1-desoxynojirimycin
N-Undecyl-1-desoxynojirimycin
N-Dodecyl-1-desoxynojirimycin
N-Tetradecyl-1-desoxynojirimycin
N-(5-Hydroxypentyl)-1-desoxynojirimycin
N-Cyclohexylmethyl-1-desoxynojirimycin
N-(Cyclohex-3-enylmethyl)-1-desoxynojirimycin
N-(Bicyclo[2.2.2]oct-2-ylmethyl)-1-desoxynojirimycin
N-p-Chlorobenzyl-1-desoxynojirimycin
N-m-Methylbenzyl-1-desoxynojirimycin
N-(4-Bisphenylmethyl)-1-desoxynojirimycin
N-(3-Phenylpropyl)-1-desoxynojirimycin
N-Allyl-1-desoxynojirimycin
N-(2-Propinyl)-1-desoxynojirimycin
N-(3,4-Dichlorobenzyl)-1-desoxynojirimycin
N-(4-Nitrobenzyl)-1-desoxynojirimycin
(N-(3-Nitrobenzyl)-1-desoxynojirimycin
1-Cyano-1-desoxynojirimycin
N-Methyl-1-cyano-1-desoxynojirimycin
1-Desoxynojirimycin-1-carboxylic acid
1-Ethoxycarbonyl-1-desoxynojirimycin
N-Methyl-1-ethoxycarbonyl-1-desoxynojirimycin
1-Desoxynojirimycin-1-carboxamide
N-Benzyl-1-desoxynojirimycin-1-carboxamide
N'-Methyl-N-benzyl-1-desoxynojirimycin-1-carboxamide
1-Aminomethyl-1-desoxynojirimycin
1-Acetamidomethyl-1-desoxynojirimycin
N-Methyl-1-acetylaminomethyl-1-desoxynojirimycin
1-Benzoylaminomethyl-1-desoxynojirimycin
N-Methyl-1-benzoylaminomethyl-1-desoxynojirimycin
1-p-Toluenesulphonylaminomethyl-1-desoxynojirimycin
N-Methyl-1-p-Toluenesulphonylaminomethyl-1-desoxynojirimycin
1-(N'-Phenylureidomethyl)-1-desoxynojirimycin
N,6-(1-desoxynojirimycinyl)acetolactone
N-Benzyl-(1-desoxynojirimycinyl)acetamide
N-Butyl-(1-desoxynojirimycinyl)acetamide
1-Hydroxymethyl-1-desoxynojirimycin
6-0-Benzoyl-1-desoxynojirimycin
N-(2-Methoxyethyl)-1-desoxynojirimycin
N-(2-Methylthioethyl)-1-desoxynojirimycin
N-(2-Ethylthio)-1-desoxynojirimycin
N-[2-(2-Methoxyethoxy)ethyl]-1-desoxynojirimycin
N-Nonyl-1-acetylaminomethyl-1-desoxynojirimycin
1-Nonylaminomethyl-1-desoxynojirimycin
N-Phenyl-1-desoxynojirimycin
N-Cyclohexyl-1-desoxynojirimycin
N-Isopropyl-1-desoxynojirimycin
N-(1-Desoxyglucityl)-1-desoxynojirimycin N-(2-Phenoxyethyl)-1-desoxynojirimycin
N-(5-Phenoxypentyl)-1-desoxynojirimycin
N-(4-Phenoxybutyl)-1-desoxynojirimycin
N-(2-(2,6-Xylyloxy)ethyl)-1-desoxynojirimycin
N-(3-(2,6-Xylyloxy)propyl)-1-desoxynojirimycin
N-(2-(2,4-Dichlorophenoxy)ethyl-1-desoxynojirimycin
N-(4-Phenoxy-2-butenyl)-1-desoxynojirimycin
N-[4-(4-Tolyloxy)-2-butenyl]-1-desoxynojirimycin
N-[4-(4-Ethoxycarbonylphenoxy)-2-butenyl]-1-desoxynojirimycin
N-[2-(4-Methoxyphenoxy)ethyl]-1-desoxynojirimycin
N-[2-(4-Chlorophenoxy)ethyl]-1-desoxynojirimycin
N-[2-(4-Cyanophenoxy)ethyl]-1-desoxynojirimycin
N-[2-(3-Tolyloxy)ethyl]-1-desoxynojirimycin
N-(2-Phenylthioethyl)-1-desoxynojirimycin
N-[2-(4-Tolylthio)ethyl]-1-desoxynojirimycin
N-[4-(3-Tolylthio)-2-butenyl]-1-desoxynojirimycin
N-[4-(4-Chlorophenylthio)-2-butenyl]-1-desoxynojirimycin
N-[4-(tert.-Butylphenylthio)-2-butenyl]-1-desoxynojirimycin
N-[4-(4-Tolylthio)-2-butenyl]-1-desoxynojirimycin
N-[4-(4-Biphenylyloxy)-2-butenyl]-1-desoxynojirimycin
N-(3-Butenyl)-1-desoxynojirimycin
N-(2,4-Hexadienyl)1-desoxynojirimycin
N-(2,4-Heptadienyl)-1-desoxynojirimycin
N-Cinnamyl-1-desoxynojirimycin
N-(2-Pentenyl)-1-desoxynojirimycin
N-(2-Butenyl)-1-desoxynojirimycin
N-(8,8-Dimethyl-2-nonenyl)-1-desoxynojirimycin.

In the context of investigations which led to the present invention, it was surprisingly found that the above-mentioned compounds of the general formula (I) are antivirals, and are actually active against retroviruses. This is confirmed by the experimental data given further below, for example, for the compounds on Visna virus in cell culture. The Visna virus and the HIV virus (human immunodeficiency virus) both belong to the retrovirus subfamily of lentiviruses (Haase A. T., *Nature*, (1986), 322, 130–136). Both viruses exhibit a similar genome organization and a complex transcription pattern compared to the other retroviruses (Sonijo P. et al., *Cell*, (1985), 42, 369–382; Davis J. L. et al., *Journal of Virology*, (1987), 61, (5), 1325–1331.

In cell cultures which are infected with Visna virus, pronounced, virus-induced, cytopathic effects appear 5 to 10 days after infection. By treating the infected cell cultures with the compounds according to the invention, the appearance of these cytopathic effects could be prevented. Since they influence the glycosylation pattern of the virus proteins, the compounds according to the invention can be used for the production of attenuated or non-infectious virus particles, which in turn can be employed for vaccine production. The Visna virus test was carried out according to the method of O. Narayan et al., *Journal of Infectious Diseases*, 135, 5, (1977), 800–806. For this, the compound according to the invention was diluted to non-cytotoxic concentrations in the culture medium in 96 well microtiter plates. Sheep fibroblast cells ($5\times10^4$ cells per well) in production medium were then added to each well. To each well then was added 50 $\mu$l of a Visna virus solution having a titre of about $2.5\times10^4$ $TCID_{50}$ (TCID = tissue culture infectious dose).

This virus dose corresponds to an MOI (multiplicity of infection) of about 0.05.

Under these infection conditions, a virus-induced, cytopathic effect resulted between Day 5 and Day 10 in the infection control without testing-substance. The infected and treated cells and the control cells were incubated for 7–9 days at 37° C. and 5% $CO_2$.

On appearance of the virus-induced, cytopathogenic effect in the untreated virus control, the cultures were fixed with formalin and then coloured with a Giemsa solution. The inhibitory concentration ($IC_{50}$) was microscopically determined as the concentration at which the cytopathic effect was inhibited by 50% in comparison to the untreated virus control which exhibited 100% cell destruction.

It was found that, for example N-(2-butenyl-1-desoxynojirimycin) in a concentration range of 500 $\mu$g/ml to 30 $\mu$g/ml protected the cells infected with Visna virus from the virus induced cell destruction.

Similar protective effects could be observed on application of N-(Prop-1-en-3yl)-1-desoxynojirimycin and N-(1-Phenyl-prop-1en-3yl)-1-desoxynojirimycin as depicted in table 1.

| Compound No. | $Ic_{50}/\mu g/ml$ |
|---|---|
| 1 | 30 |
| 2 | 100 |
| 3 | 50 |
| 4 | 250 |
| 5 | 50 |
| 6 | 30 |
| 7 | 10 |
| 8 | 10 |
| 9 | 10 |
| 10 | 20 |

1 N-(2-Butenyl)-1-desoxynojirimycin
2 N-(4-(4-Methylphenylthio)-buten-2yl)-1-desoxynojirimycin
3 N-Amino-1-desoxynojirimycin
4 2-Hydroxymethyl-3,4,5-trihydroxy-6-butylpiperidine
5 N-(Prop-1-en-3yl)-1-desoxynojirimycin
6 N-(1-Phenyl-prop-1en-3yl)-1-desoxynojirimycin
7 N-Ethyl-1-desoxynojirimycin
8 N-Methyl-1-desoxynojirimycin
9 N-Butyl-1-desoxynojirimycin
10 N-Propyl-1-desoxynojirimycin The compounds to be used according to the invention therefore represent valuable active compounds in human and veterinary medicine for the treatment and prophylaxis of diseases caused by retroviruses.

Indication areas which may be mentioned in human medicine are, for example:

1. The treatment or prophylaxis of human retrovirus infections.
2. The treatment or prophylaxis of diseases (AIDS) caused by HIV (human immunodeficiency virus; formerly named HTLV III/LAV) and the stages associated therewith such as ARC (AIDS-related complex) and LAS (lymphadenopathy syndrome) and also the hypoimmunity and encephalopathy caused by this virus.
3. The treatment or the prophylaxis of a HTLV I or HTLV II infection.
4. The treatment of the prophylaxis of the AIDS carrier condition.

Indications in veterinary medicine which may be mentioned are, for example:

Infections with a) Maedivisna (in sheep and goats)
b) progressive pneumonia virus (PPV) (in sheep and goats)
c) caprine arthritic encephalitis virus (in sheep and goats)

d) Zwoegerziekte virus (in sheep)
e) infectious anaemia virus (of the horse)
f) infections caused by feline T-cell leukaemia virus.

The present invention includes pharmaceutical preparations which consist of one or more compounds of the formula (I) in addition to non-toxic, inert pharmaceutically acceptable excipients, and processes for the production of these preparations.

The present invention also includes pharmaceutical preparations in dosage units. This means that the preparations are in the form of individual portions, for example tablets, dragees, capsules, pills, suppositories and ampoules, whose active compound content corresponds to a fraction or a multiple of an individual dose. The dosage units may contain, for example, 1, 2, 3 or 4 individual doses or ½, ⅓ or ¼ of an individual dose. An individual dose preferably contains the amount of active compound which is administered in one application and which usually corresponds to a whole, a half or a third or a quarter of a daily dose.

Non-toxic, inert pharmaceutically suitable excipients are taken to mean solid, semi-solid or liquid diluents, fillers or formulation auxiliaries of any type.

Preferred pharmaceutical preparations which may be mentioned are tablets, dragees, capsules, pills, granules, suppositories, solutions, suspensions and emulsions, pastes, ointments, gels, creams, lotions, powders and sprays.

Tablets, dragees, capsules, pills and granules may contain the active compound(s) in addition to the customary excipients, such as (a) fillers and extenders, for example, starches, lactose, sucrose, glucose, mannitol and silica, (b) binders, for example, carboxymethylcellulose, alginates, gelatin, polyvinylpyrrolidone, (c) humectants, for example, glycerol, (d) disintegrants, for example, agar-agar, calcium carbonate and sodium bicarbonate, (e) solution retardants, for example, paraffin and (f) absorption accelerators, for example, quaternary ammonium compounds, (g) wetting agents, for example, cetyl alcohol, glycerol monostearate, (h) adsorption agents, for example, kaolin and bentonite and (i) lubricants, for example, talc, calcium stearate and magnesium stearate and solid polyethylene glycols or mixtures of the substances mentioned under (a) to (i).

The tablets, dragees, capsules, pills and granules may be provided with the customary coatings and shells containing, if appropriate, opacifying agents and may be so composed that they release the active compound, if appropriate with a delay, only or preferably in a certain section of the intestinal tract, using, for example, polymeric substances and waxes as embedding materials.

If appropriate, the active compound(s) may also be present in microencapsulated form with one or more of the abovementioned excipients.

In addition to the active compound(s), suppositories may contain the customary water-soluble or water-insoluble excipients, for example, polyethylene glycols, fats, for example, cocoa fat and higher esters (for example, $C_{14}$-alcohol with $C_{16}$-fatty acid) or mixtures of these substances.

In addition to the active compound(s), ointments, pastes, creams and gels may contain the customary excipients, for example, animal and vegetable fats, waxes, paraffins, starch, tragacanth, cellulose derivatives, polyethylene glycols, silicones, beutoniles, silica, talc and zinc oxide or mixtures of these substances.

Powders and sprays may contain the customary excipients in addition to the active compound(s), for example, lactose, talc, silica, aluminium hydroxide, calcium silicate and polyamide powder or mixtures of these substances. Sprays may additionally contain the customary propellants, for example chlorofluorohydrocarbons.

Solutions and emulsions may contain the customary excipients, such as solvents, solution retardants and emulsifiers, for example, water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, groundnut oil, corn germ oil, olive oil, castor oil and sesame oil, glycerol, glycerol formal, tetrahydrofurfuryl alcohol, polyethylene glycol and fatty acid esters of sorbitan or mixtures of these substances in addition to the active compound(s).

For parenteral administration, the solutions and emulsions may also be present in sterile and blood-isotonic form.

Suspensions may contain the customary excipients, such as liquid diluents, for example, water, ethyl alcohol, propylene glycol, suspending agents, for example, ethoxylated isostearyl alcohols, polyoxyethylene sorbitol and sorbitan esters, microcrystalline cellulose, aluminium metahydroxide, bentonite, agar-agar and tragacanth or mixtures of these substances in addition to the active compound(s).

The formulation forms mentioned may also contain colourants, preservatives and also odor-improving and flavor-improving additives, for example, peppermint oil and eucalyptus oil and sweeteners, for example saccharin.

The active compounds fo the formula (I) should preferably be present in the abovementioned pharmaceutical preparations in a concentration of about 0.1 to 99.5, preferably 0.5 to 95% by weight, of the total mixture.

The abovementioned pharmaceutical preparations can also contain additional pharmaceutical active compounds in addition to the compounds of the formula (I).

The preparation of the abovementioned pharmaceutical preparations takes place in a customary manner by known methods, for example by mixing the active compound(s) with the excipient(s).

The preparations mentioned may either be used in humans and animals orally, rectally, parenterally (intravenously, intramuscularly, subcutaneously), intracisternally, intravaginally, intraperitoneally, locally (powder, ointment, drops) and for the therapy of infections in hollow spaces and body cavities. Suitable preparations are injection solutions, solutions and suspensions for oral treatment, gels, pour-on formulations, emulsions, ointments or drops. For local treatment, ophthalmological and dermatological formulations, silver and other salts, ear drops, eye ointments, powders or solutions may be used. In animals, the administration can also take place in suitable formulations via the feed or drinking water. Furthermore, gels, powders, tablets, delayed-release tablets, premixes, concentrates, granules, pellets, tablets, boli, capsules, aerosols, sprays and inhalants may be used in humans and animals. Furthermore, the compounds according to the invention may be incorporated into other excipient materials such as, for example, plastics, (plastic chains for local therapy), collagen or bone cement.

In general, it has proved advantageous both in human and veterinary medicine to administer the active compound(s) of the formula (I) in total amounts of about 0.5 to about 500, preferably 5 to 100 mg/kg of body weight every 24 hours, if appropriate in the form of several individual doses, to obtain the desired results. An individual dose preferably contains the active compound(s) in amounts from about 1 to about 80, in particular 3 to 30 mg/kg of body weight. However, it may be necessary to deviate from the dosages mentioned, depending upon the species and the body weight of the subject to be treated, the nature and the severity of the disease, the type of the preparation and the administration of the medicament and also the time period or interval within which the administration takes place.

Thus, in some cases it may be sufficient to manage with less than the abovementioned amount of active compound, whereas in other cases the abovementioned amount of active compounds must be exceeded. The optimum dosage required in each case and type of administration of the active compounds can easily be established by one skilled in the art on the basis of his expert knowledge.

The compounds to be used according to the invention may be given together with the food or with the food preparations or with the drinking water in the customary concentrations and preparations.

It will be appreciated that the instant specification and claims are set forth by way of illustration and not limitation, and that various modifications and changes may be made without departing from the spirit and scope of the present invention.

What is claimed is:

1. A method for treating a viral infection in a human or animal patient comprising administering to said patient an antivirally effective amount of a 2-hydroxymethylene-3,4,5-trihydroxypiperidine or a pharmaceutically acceptable salt thereof of the formula (I)

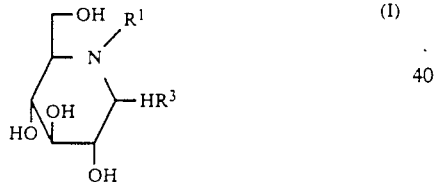

in which
R$^1$ stands for hydrogen and
R$^3$ stands for an unsubstituted or substituted straight-chain, branched or cyclic, saturated or unsaturated hydrocarbon radical which is not interrupted or interrupted by heteroatoms selected from the group consisting of N, O and S, an unsubstituted or substituted aromatic radical or an unsubstituted or substituted heterocyclic radical, or in which
R$^1$ stands for hydrogen or for an unsubstituted or substituted, straight-chain, branched or cyclic, saturated or unsaturated hydrocarbon radical, or for an unsubstituted or substituted aromatic or heterocyclic radical and
R$^3$ stands for —H, OH, —OR$^5$, —SH, SR$^5$, —NH$_2$, —NHR$^5$,

NH$_2$CH$_2$—, NHR$^5$—CH$_2$—, NR$^5$R$^4$—CH$_2$—, —COOH, —COOR$^5$, HO—CH$_2$—, R$^5$CO—NHCH$_2$—, R$^5$CO—CR$^4$CH$_2$—, R$^5$SO$_2$NHCH$_2$—, R$^5$SO$_2$—NR$^4$CH$_2$—,

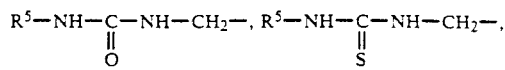

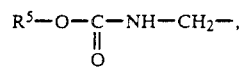

—SO$_3$H, —CN, —CONH$_2$, CONHR$^5$ or CONR$^5$R$^4$ where
R$^5$ and R$^4$ can assume the meanings previously mentioned for R$^1$, and where for the case in which R$^3$=H or OH, R$^1$ stands for an unsubstituted or substituted, straight-chain, branched or cyclic, saturated or unsaturated hydrocarbon radical or for an unsubstituted or substituted aromatic or heterocyclic radical or in which
R$^1$ stands for

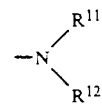

wherein
R$^{11}$ denotes hydrogen, —formyl, —R$^{14}$, —COR$^{14}$, CO$_2$R$^{14}$, CONH$_2$, CONHR$^{14}$, CONR$^{14}$R$^{15}$, CSR$^{14}$, CSNH$_2$, CSNHR$^{14}$, CSNR$^{14}$R$^{15}$, SO$_3$H or SO$_2$R$^{14}$,
R$^{12}$ denotes hydrogen or R$^{14}$ or
R$^{11}$ and R$^{12}$ together denote the grouping

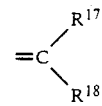

R$^3$ denotes hydrogen, hydroxyl, OR$^{14}$, mercapto, SR$^{14}$, amino, NHR$^{14}$, NR$^{14}$R$^{15}$, cyano, carboxyl, CO$_2$R$^{14}$, carboxylamido, CONHR$^{14}$, CONR$^{14}$R$^{15}$, aminomethyl, CH$_2$NHR$^{14}$, CH$_2$NR$^{14}$R$^{15}$, CH$_2$—NR$^{14}$COR$^{15}$, CH$_2$NR$^{14}$SO$_2$R$^{15}$, sulpho, hydroxymethyl, CH$_2$OR$^{14}$ or CH$_2$OCOR$^{14}$, and
R$^{14}$ and R$^{15}$ independently of one another denote an unsubstituted or substituted, straight-chain, branched or cyclic, saturated or unsaturated aliphatic hydrocarbon radical or an unsubstituted or substituted aromatic or heterocyclic radical, where two radicals R$^{15}$, R$^{17}$ and R$^{18}$ can also be bonded with one another, and
R$^{17}$ and R$^{18}$ independently of one another denote hydrogen or R$^{15}$ or in which
R$^3$ stands for hydrogen and
R$^1$ stands for

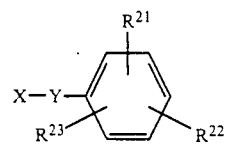

wherein
X stands for a straight-chain or branched saturated or unsaturated hydrocarbon radical,
Y stands for oxygen or sulphur and
$R^{21}$, $R^{22}$ and $R^{23}$ are identical or different and independently of one another stand for hydrogen, halogen, alkyl, aryl, alkoxy, aroxy, alkylthio, nitro, amino, hydroxyl, cyano, alkylamino and dialkylamino, acylamino, acyloxy, carboxyl, carbalkoxy, alkylcarbonyl, formyl or an unsubstituted or substituted sulphonamide radical.

2. A method according to claim 1, wherein for $R^3$, the hydrocarbon radical is selected from the group consisting of $C_1$–$C_{30}$-alkyl, $C_2$–$C_{18}$-alkenyl, $C_2$–$C_{18}$-alkinyl, $C_3$–$C_{12}$-cycloalkyl, $C_3$–$C_{12}$-cycloalkenyl, $C_3$–$C_{12}$-cycloalkadienyl, $C_3$–$C_{12}$-bicycloalkyl, $C_3$–$C_{12}$-bicycloalkenyl, $C_3$–$C_{12}$-bicycloalkadienyl, $C_3$–$C_{12}$-tricycloalkenyl, $C_3$–$C_{12}$-tricycloalkadienyl, phenyl, naphthyl, $C_3$–$C_7$-heterocycles having 1 to 4 carbon atoms and a heteroatom selected from the group consisting of N, O and S, onto which is or is not condensed a benzene radical.

3. A method according to claim 1, wherein for $R^1$, the hydrocarbon radical is selected from the group consisting of $C_1$–$C_{18}$-alkyl, unsubstituted or substituted by 1 to 5 halogen atoms, $C_3$–$C_{10}$-alkenyl, $C_3$–$C_{10}$-alkinyl, $C_3$–$C_7$-cycloalkyl and phenyl which is unsubstituted or substituted by a substituent selected from the group consisting of halogen, $C_1$–$C_4$-alkyl, $C_1$–$C_4$-alkoxy and nitro.

4. A method according to claim 1, wherein $R^1$, $R^5$ and $R^4$, independently of one another denote an alkyl radical having 1 to 18 C atoms; an alkenyl radical or alkinyl radical having 3 to 10 C atoms; a mono-, bi- or tricyclic radical having 3 to 10 C atoms, which is saturated or mono-unsaturated or diunsaturated, an aryl radical having 6 to 10 C atoms, a heterocyclic radical having 3 to 6 ring members, which can contain 1, 2, 3 or 4 heteroatoms, said heteroatoms being selected from the group consisting of N, O and S, and onto which can be condensed a benzene ring or an additional heterocycle, where the radicals mentioned can carry 1, 2 or 3 substituents, wherein the substituents for alkyl are hydroxyl or alkoxy having 1 to 4 carbon atoms, acyloxy, where the acyl radical is derived from aliphatic carboxylic acids having 1 to 7 C atoms, aromatic carboxylic acids, which are unsubstituted or substituted in the phenyl radical by —OH, —halogen, $C_1$–$C_4$-alkyl, $C_1$–$C_4$-alkoxy, nitro and/or amino heterocyclic carboxylic acids which are derived from 5- or 6-membered heterocycles which contain 1 to 3 heteroatoms and are unsubstituted or substituted in the heterocyclic ring by $C_1$–$C_4$-alkyl, chlorine, bromine or amino; amino, monoalkylamino and dialkylamino having 1 to 4 carbon atoms per alkyl radical, monoacylamino, where the acyl radical is derived from aliphatic carboxylic acids having 1 to 7 C atoms, aromatic carboxylic acids, which are unsubstituted or substituted in the aromatic part by —OH, —halogen, $C_1$–$C_4$-alkyl, $C_1$–$C_4$-alkoxy, nitro and/or amino, heterocyclic carboxylic acids which are derived from 5- or 6-membered heterocycles containing 1 to 3 heteroatoms and which are unsubstituted or substituted in the heterocyclic ring by $C_1$–$C_4$-alkyl, chlorine, bromine or amino.

5. A method according to claim 1, wherein
$R^{14}$ and $R^{15}$ denote alkyl having 1 to 30 C atoms, alkenyl or alkinyl having 2 to 18 C atoms, mono-, bi- or tricyclo-alkyl, -alkenyl or -alkadienyl having 3 to 10 C atoms, aryl having 6 to 10 C atoms, a heterocyclic radical having 3 to 8 ring members, which contain 1, 2, 3 or 4 heteroatoms, and onto which can be condensed a benzene ring or an additional heterocycle, where the radicals mentioned are unsubstituted or carry 1 to 5 substituents.

6. A method according to claim 1, wherein
$R^3$ stands for hydrogen, hydroxyl, sulpho, cyano, aminomethyl, $C_1$–$C_6$-alkylaminomethyl and $C_1$–$C_6$-alkylcarbonylaminomethyl and $R^4$ denotes hydroxymethyl, hydroxy($C_1$–$C_5$-alkyl)-methyl, $C_1$–$C_7$-alkyl and $C_1$–$C_5$-alkoxymethyl.

7. A method according to claim 1, in which
$R^1$ stands for

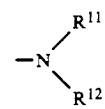

wherein
$R^{11}$ denotes hydrogen, $C_1$–$C_4$-alkyl, $C_1$–$C_4$-alkoxy, $C_1$–$C_4$-alkylsulphony, $C_1$–$C_4$-alkylcarbonyl or -phenyl, $R^{12}$ denotes hydrogen, $C_1$–$C_{12}$-alkyl which is unsubstituted or substituted by hydroxyl, $C_1$–$C_4$-alkoxy, carboxyl, $C_5$–$C_7$-cycloalkyl or phenylsulphonylamino, $C_2$–$C_4$-alkenyl, phenyl which is unsubstituted or substituted in the phenyl ring by halogen, $C_1$–$C_4$-alkyl, hydroxyl, di-$C_1$–$C_4$-alkylamino or $C_1$–$C_4$-alkoxy, phenyl-$C_1$–$C_4$-alkyl or benzoylmethyl, $C_5$–$C_7$-cycloalkyl, furylmethyl, pyridylmethyl or diphenylmethyl or $R^1$ and $R^2$ together denote a grouping

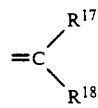

wherein
$R^{18}$ denotes hydrogen, $C_1$–$C_{12}$-alkyl which is unsubstituted or substituted by hydroxyl, $C_1$–$C_4$-alkoxy or phenylsulphonylamino, $C_5$–$C_7$-cycloalkyl, $C_2$–$C_{12}$-alkenyl, carboxyl, phenyl which is unsubstituted or substituted by halogen, $C_1$–$C_4$-alkyl, hydroxyl, nitro, di-$C_1$–$C_4$-alkylamino, $C_1$–$C_4$-alkoxy or $C_1$–$C_4$-carboxyl, phenyl-$C_1$–$C_4$-alkyl or phenyl-$C_1$–$C_4$-benzoyl, furyl, pyridyl or together with $R_7$ and the double bonded C atom denote a cyclopentane or cyclohexane ring and
$R^{17}$ has the meaning of $R^{11}$, and
$R^3$ denotes hydrogen, $C_1$–$C_6$-alkylcarbonylaminomethyl, phenylcarbonylaminomethyl, phenylsulphonylaminomethyl, $C_1$–$C_4$-alkoxycarbonyl and $C_1$–$C_6$-alkylaminocarbonyl.

8. A method according to claim 1, wherein $R^{21}$, $R^{22}$ and $R^{23}$, independently of each other denote hydrogen, alkyl, alkoxy or halogen.

9. A method according to claim 1, wherein the 2-hydroxymethylene-3,4,5-trihydroxypiperidine is selected from the group consisting of
N-(2-Vinylsulphonylethyl)-1-desoxynojirimycin,
N-Undecen-10-yl-1-desoxynojirimycin,
1-(N'-5-Cyanopentylureidomethyl)-1-desoxynojirimycin,
N-(Hexa-2,4-dienyl)-1-desoxynojirimycin,
N-Methyl-1-desoxynojirimycin, N-Butyl-1-desoxynojirimycin,
N-Ethyl-1-desoxynojirimycin,
N-Propyl-1-desoxynojirimycin,
N-Isobutyl-1-desoxynojirimycin,
N-Heptyl-1-desoxynojirimycin,
N-Benzyl-1-desoxynojirimycin,
N-(2-Pyridylmethyl)-1-desoxynojirimycin,
N-(2-Hydroxyethyl)-1-desoxynojirimycin,
N-(2,3-Dihydroxypropyl)-1-desoxynojirimycin,
N-[2-(s-$\beta$-D-Glucopyranosylthio)ethyl]-1-desoxynojirimycin,
N-(2,3-Epoxypropyl)-1-desoxynojirimycin,
N-[3-Phthalimidopropyl]-1-desoxynojirimycin,
N-(3-Aminopropyl)-1-desoxynojirimycin,
N-(1-Desoxynojirimycin-yl)acetic acid,
N-o-Nitrobenzyl-1-desoxynojirimycin,
N-o-Carboxybenzyl-1-desoxynojirimycin,
N-p-Sulphobenzyl-1-desoxynojirimycin,
N-Phenylethyl-1-desoxynojirimycin,
N-Pentyl-1-desoxynojirimycin,
N-Hexyl-1-desoxynojirimycin,
N-Octyl-1-desoxynojirimycin,
N-Nonyl-1-desoxynojirimycin,
N-(3-Butenyl)-1-desoxynojirimycin,
N-(2,4-Hexadienyl)-1-desoxynojirimycin,
N-(2,4-Heptadienyl)-1-desoxynojirimycin,
N-Cinnamyl-1-desoxynojirimycin,
Decyl-1-desoxynojirimycin,
undecyl-1-desoxynojirimycin,
dodecyl-1-desoxynojirimycin,
tetradecyl-1-desoxynojirimycin,
5-Hydroxypentyl-1-desoxynojirimycin,
Cyclohexylmethyl-1-desoxynojirimycin,
4-Cyclohex-3-enylmethyl)-1-desoxynojirimycin,
4-Bicyclo[2.2.2]oct-2-ylmethyl)-1-desoxynojirimycin,
N-p-Chlorobenzyl-1-desoxynojirimycin,
N-m-Methylbenzyl-1-desoxynojirimycin,
N-(4-Biphenylmethyl)-1-desoxynojirimycin,
N-(3-Phenylpropyl)-1-desoxynojirimycin,
N-Allyl-1-desoxynojirimycin,
N-(2-Propinyl)-1-desoxynojirimycin,
N-(3,4-Dichlorobenzyl)-1-desoxynojirimycin,
N-(4-Nitrobenzyl)-1-desoxynojirimycin,
(N-(3-Nitrobenzyl)-1-desoxynojirimycin,
1-Cyano-1-desoxynojirimycin,
N-Methyl-1-cyano-1-desoxynojirimycin,
1-Desoxynojirimycin-1-carboxylic acid,
1-Ethoxycarbonyl-1-desoxynojirimycin,
N-Methyl-1-ethoxycarbonyl-1-desoxynojirimycin,
1-Desoxynojirimycin-1-carboxamide,
N'-Benzyl-1-desoxynojirimycin-1-carboxamide,
N-Methyl-N'-benzyl-1-desoxynojirimycin-1-carboxamide,
1-Aminomethyl-1-desoxynojirimycin,
1-Acetylaminomethyl-1-desoxynojirimycin,
N-Methyl-1-acetylaminomethyl-1-desoxynojirimycin,
1-Benzylaminomethyl-1-desoxynojirimycin,
N-Methyl-1-benzoylaminomethyl-1-desoxynojirimycin,
1-p-Toluenesulphonylaminomethyl-1-desoxynojirimycin,
N-Methyl-1-p-toluenesulphonylaminomethyl-1-desoxynojirimycin,
1-(N'-Phenylureidomethyl)-1-desoxynojirimycin,
N,6-(1-Desoxynojirimycinyl)acetolactone
N'-Benzyl-(1-desoxynojirimycinyl)acetamide,
N'-Butyl-(1-desoxynojirimycinyl)acetamide,
1-Hydroxymethyl-1-desoxynojirimycin,
6-O-Benzoyl-1-desoxynojirimycin, N-(2-Methoxyethyl)-1-desoxynojirimycin,
N-(2-Methylthioethyl)-1-desoxynojirimycin,
N-(2-Ethylthio)-1-desoxynojirimycin,
N-[2-(2-Methoxyethoxy)ethyl]-1-desoxynojirimycin,
N-Nonyl-1-acetylaminomethyl-1-desoxynojirimycin,
1-Nonylaminomethyl-1-desoxynojirimycin,
N-Phenyl-1-desoxynojirimycin,
N-Cyclohexyl-1-desoxynojirimycin,
N-Isopropyl-1-desoxynojirimycin,
N-(1-Desoxyglucityl)-1-desoxynojirimycin,
N-(2-Phenoxyethyl)-1-desoxynojirimycin,
N-(5-Phenoxypentyl)-1-desoxynojirimycin,
N-(4-Phenoxybutyl)-1-desoxynojirimycin,
N-(2-(2,6-Xylyloxy)ethyl)-1-desoxynojirimycin,
N-(3-(2,6-Xylyloxy)propyl)-1-desoxynojirimycin,
N-(2-(2,4-Dichlorophenoxy)ethyl-1-desoxynojirimycin,
N-(4-Phenoxy-2-butenyl)-1-desoxynojirimycin,
N-[4-(4-tolyloxy)-2-butenyl]-1-desoxynojirimycin,
N-[4-(4-Ethoxycarbonylphenoxy)-2-butenyl]-1-desoxynojirimycin,
N-[2-(4-Methoxyphenyl)ethyl]-1-desoxynojirimycin,
N-[2-(4-Chlorophenoxy]ethyl]-1-desoxynojirimycin,
N-[2-(4-Cyanophenoxy)ethyl]-1-desoxynojirimycin,
N-[2-(3-tolyloxy)ethyl]-1-desoxynojirimycin,
N-(2-Phenylthioethyl)-1-desoxynojirimycin,
N-2-(4-Tolylthio)ethyl)-1-desoxynojirimycin,
N-[4-(3-Tolylthio)-2-butenyl]-1-desoxynojirimycin,
N-[4-(4-Chlorophenylthio)-2-butenyl]-1-desoxynojirimycin,
N-[4-(tert.-Butylphenylthio)-2-butenyl]-1-desoxynojirimycin,
N-[4-(4-Tolythio)-2-butenyl]-1-desoxynojirimycin,
N-[4-(4-Biphenylyloxy)-2-butenyl]-1-desoxynojirimycin,
N-(2-Pentenyl)-1-desoxynojirimycin,
N-(2-Butenyl)-1-desoxynojirimycin,
N-(8,8-Dimethyl-2-nonenyl)-1-desoxynojirimycin,
N-$\beta$-Phenoxyethyl-1-desoxynojirimycin,
N-(5-Phenoxypentyl)-1-desoxynojirimycin,
N-(4-Phenoxybutyl)-1-desoxynojirimycin,
N-[$\beta$-(2,6-Dimethylphenoxy)ethyl]-1-desoxynojirimycin,
N-[$\gamma$-(2,6-Dimethoxyphenoxy)propyl]-1-desoxynojirimycin,
N-[$\beta$-(2,4-Dichlorophenoxy)ethyl]-1-desoxynojirimycin,
N-($\gamma$-Phenoxypropyl)-1-desoxynojirimycin,
N-(4-Phenoxy-trans-buten-2-yl)-1-desoxynojirimycin hydrate,
N-(p-Methoxyphenyloxy-trans-buten-2-yl)-1-desoxynojirimycin,
N-[(4-Carbethoxyphenyloxy)-buten-2-yl]-1-desoxynojirimycin,
N-[$\beta$-(4-Methoxyphenoxy)ethyl]-1-desoxynojirimycin,
N-[$\beta$-(4-Chlorophenoxy)ethyl]-1-desoxynojirimycin,
N-[$\beta$-(4-Cyanophenoxy)ethyl]-1-desoxynojirimycin,
N-[$\beta$-(3-Methylphenoxy)ethyl]-1-desoxynojirimycin,
N-($\beta$-Phenylthioethyl)-1-desoxynojirimycin,
N-[$\beta$-(4-Methylphenylthio)ethyl]-1-desoxynojirimycin,
N-[4-(4-Methylphenylthio)buten-2-yl]-1-desoxynojirimycin,
N-[4-(4-Chlorophenylthio)buten-2-yl]-1-desoxynojirimycin,
N-[4-(4-tert.-Butylphenylthio)buten-2-yl]-1-desoxynojirimycin,
N-[4-(4-Methylphenylthio)buten-2-yl]-1-desoxynojirimycin, N-[4-(4-Phenylphenoxy)buten-2-yl]-1-desoxynojirimycin,
N-[β-(4-Acetamidophenoxy)ethyl]-1-desoxynojirimycin,
N-[β-(4-Ethoxycarbonylphenoxy)ethyl]-1-desoxynojirimycin,
N-[β-(4-Formylphenoxy)ethyl]-1-desoxynojirimycin,
N-[β-(4-Hydroxyphenoxy)ethyl]-1-desoxynojirimycin,
N-[β-(3-Ethoxycarbonylphenoxy)ethyl]-1-desoxynojirimycin,
N-[4-(4-Acetamidophenoxy)buten-2-yl]-1-desoxynojirimycin hydrate,
N-[β-(4-Aminomethylphenoxy)ethyl]-1-desoxynojirimycin,
N-[β-(4-Hydroxymethylphenoxy)ethyl]-1-desoxynojirimycin,
N-[4-(4-Aminophenoxy)but-2-en-yl]-1-desoxynojirimycin,
N-[β-(4-Aminophenoxy)ethyl]-1-desoxynojirimycin,
N-[β-(4-Hydroxycarbonylphenoxy)ethyl]-1-desoxynojirimycin,
N-[β-(3-Hydroxycarbonylphenoxy)ethyl]-1-desoxynojirimycin,
N-[β-(4-tert.-Butylphenylthio)ethyl]-1-desoxynojirimycin,
N-(4-Phenylthiobuten-2-yl)-1-desoxynojirimycin,
N-[β-(4-Cyanomethylphenoxy)ethyl]-1-desoxynojirimycin,
N-[β-(4-Aminoethylphenoxy)ethyl]-1-desoxynojirimycin,
N-[β-(4-Succinimidyloxycarbonyl)ethyl]-1-desoxynojirimycin,
N-[β-(4-Carbamoylphenoxy)ethyl]-1-desoxynojirimycin,
N-[β-(4-Morpholinocarbonylphenoxy)ethyl]-1-desoxynojirimycin,
N-[2-(4-Phenylcarbamoylphenoxy)ethyl]-1-desoxynojirimycin,
N-[2-(4-Phenylphenoxy)ethyl]-1-desoxynojirimycin,
N-Amino-1-desoxynojirimycin,
N-(Benzylideneamino)-1-desoxynojirimycin,
N-(2-Hydroxy-3-methoxybenzylideneamino)-1-desoxynojirimycin,
N-(3-Nitrobenzylidene)amino-1-desoxynojirimycin,
N-(3-Phenylpropylidene)amino-1-desoxynojirimycin,
N-(4-Methylbenzylidene)amino-1-desoxynojirimycin,
N-(4-Methoxybenzylidene)amino-1-desoxynojirimycin,
N-(3-Cyclohexenyl)methyleneamino-1-desoxynojirimycin,
N-Undecylideneamino-1-desoxynojirimycin,
N-Heptylideneamino-1-desoxynojirimycin,
N-(Furfurylideneamino)-1-desoxynojirimycin,
N-(Thenylideneamino)-1-desoxynojirimycin,
N-(3-Pyridylmethyleneamino)-1-desoxynojirimycin,
N-(4-Chlorobenzylideneamino)-1-desoxynojirimycin,
N-(2-Methylthiobenzylideneamino)-1-desoxynojirimycin,
N-(Benzylamino)-1-desoxynojirimycin,
N-(Acetamido)-1-desoxynojirimycin,
N-(Heptylamino)-1-desoxynojirimycin,
N-(Dimethylamino)-1-desoxynojirimycin,
N-(Dioctylamino)-1-desoxynojirimycin and
2-Hydroxymethyl-3,4,5-trihydroxy-6-methylpiperidine,
2-Hydroxymethyl-3,4,5-trihydroxy-6-ethylpiperidine,
2-Hydroxymethyl-3,4,5-trihydroxy-6-propylpiperidine
2-Hydroxymethyl-3,4,5-trihydroxy-6-n-butylpiperidine,
2-Hydroxymethyl-3,4,5-trihydroxy-6-n-pentylpiperidine,
2-Hydroxymethyl-3,4,5-trihydroxy-6-n-octylpiperidine,
2-Hydroxymethyl-3,4,5-trihydroxy-6-phenylpiperidine and
2-Hydroxymethyl-3,4,5-trihydroxy-6-n-heptylpiperidine of the D-gluco configuration.

10. A method according to claim 1 wherein the viral infection is a retroviral infection.

11. A method according to claim 10, wherein the viral infection is Visna viral infection.

* * * * *

UNITED STATES PATENT AND TRADEMARK OFFICE
CERTIFICATE OF CORRECTION

PATENT NO. : 5,051,407

DATED : September 24, 1991

INVENTOR(S) : Boshagen et al.

It is certified that error appears in the above-identified patent and that said Letters Patent is hereby corrected as shown below:

Col. 22, claim 11 line 1    Delete " claim 10 " and substitute -- claim 1 --

Signed and Sealed this

Twentieth Day of July, 1993

Attest:

MICHAEL K. KIRK

Attesting Officer    Acting Commissioner of Patents and Trademarks